United States Patent [19]

Gerstein

[11] Patent Number: 5,374,420
[45] Date of Patent: Dec. 20, 1994

[54] HAIR SETTING COMPOSITIONS

[75] Inventor: Terry Gerstein, East Brunswick, N.J.

[73] Assignee: Revlon Consumer Products Corporation, New York, N.Y.

[21] Appl. No.: 7,467

[22] Filed: Jan. 22, 1993

[51] Int. Cl.$^5$ .............................................. A61K 7/11
[52] U.S. Cl. ........................... 424/70.11; 424/DIG. 1; 424/DIG. 2; 424/70.12; 424/70.16
[58] Field of Search ............. 424/71, DIG. 1, DIG. 2

[56] References Cited

U.S. PATENT DOCUMENTS

| | | | |
|---|---|---|---|
| 3,133,865 | 5/1964 | Richardson | 424/71 |
| 3,922,341 | 11/1975 | Abegg | 424/71 |
| 3,925,542 | 12/1975 | Viout | 424/47 |
| 4,164,562 | 8/1979 | Nandagiri | 424/47 |
| 4,600,530 | 7/1986 | Bartlett | 424/DIG. 1 |
| 4,732,692 | 3/1988 | Zabotto | 252/106 |
| 4,767,613 | 8/1988 | Nuber | 424/47 |
| 4,897,262 | 1/1990 | Nandagiri | 424/71 |
| 4,963,348 | 10/1990 | Bolich, Jr. et al. | 424/71 |
| 5,019,377 | 5/1991 | Torgerson | 424/70 |
| 5,066,481 | 11/1991 | Helioff | 424/47 |
| 5,094,838 | 3/1992 | Benson | 424/47 |
| 5,104,646 | 4/1992 | Bolich | 424/70 |
| 5,118,498 | 6/1992 | Helioff | 424/70 |
| 5,120,532 | 6/1992 | Wells | 424/70 |
| 5,126,126 | 6/1992 | Varaprath et al. | 424/71 |
| 5,176,898 | 1/1993 | Goldberg | 424/47 |
| 5,306,489 | 4/1994 | Goldberg et al. | 424/71 |

*Primary Examiner*—Thurman K. Page
*Assistant Examiner*—Amy L. Hulina

[57] ABSTRACT

A hairspray/hair setting composition comprising:
a) 0.001–20% of a neutralizable hair fixative resin,
b) 0.001–8% of a base, and
c) 0.001–5% of an acid surfactant precursor
in an alcohol or aqueous/alcohol carrier.

19 Claims, No Drawings

HAIR SETTING COMPOSITIONS

TECHNICAL FIELD

The invention is in the field of hairspray and hair setting compositions.

BACKGROUND OF THE INVENTION

Hairsprays and hair setting compositions are well known in the art, and popularly comprise a neutralizable resin in conjunction with a base in an alcohol or aqueous/alcohol solvent carrier. These resins contain free carboxyl groups which are at least partially neutralized by the base. Generally, the degree of resin neutralization is manipulated to achieve hairspray compositions having the desired characteristics. For example, neutralization makes resins more water soluble. If resins are highly neutralized, they may become water soluble and may, in typical cases, cause hair to absorb atmospheric moisture to become tacky and droopy. On the other hand, resins which are minimally neutralized are largely water insoluble and may lead to difficult combing, static fly away, and may form a tenacious film on hair which is difficult to remove with shampoo.

Most hairspray manufacturers neutralize resins within certain percentage ranges to achieve the balanced properties they desire in their hairspray products. However, regardless of the degree of resin neutralization, prior art products can always be improved. It is important that a hairspray apply a clear film because clarity helps impart sheen and gloss to the hair. The film should also exhibit a certain rigidity and moisture resistance which in turn provides better holding power. It is also essential that the hairspray film be easily removable from hair through normal shampoo washing. And, of course, a desireable hair texture and ease of combing should result in easy hair styling and manageability. It has most unexpectedly been discovered that the addition of an acid surfactant precursor to a hairspray formulation having balanced attributes results in a hairspray formulation with improved clarity, rigidity, hair combability, and texture without sacrificing the other desireable features.

SUMMARY OF THE INVENTION

The invention is directed to a hairspray/hair setting composition comprising:
a) 0.001–20% of a neutralizable hair fixative resin,
b) 0.001–8% of a base, and
c) 0.001–5% of an acid surfactant precursor in an alcohol or aqueous/alcohol carrier.

The invention is also directed to a method for styling hair by applying to the hair the composition of the invention.

DETAILED DESCRIPTION

The term "neutralizable hair fixative resin" means a hair fixative resin which contains at least some carboxyl groups capable of neutralization, or a resin which is rendered easier to remove during the cleansing of the hair by the inclusion of small quantities of alkali. One type of hair fixative resin in accordance with the invention is a copolymer of a lower alkyl ester of alkyl vinyl ether-maleic acid copolymer. The copolymer has a repeating unit of the following formula:

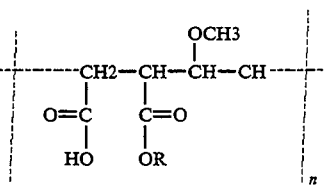

wherein R is an alkyl radical containing 1–4 carbon atoms, preferably ethyl or butyl, and n represents the repeating dimeric unit. Resins falling within the above description generally have molecular weights of 20,000–80,000. Typical resins include the monoethyl ester of methyl vinyl ethermaleic acid copolymer (commercially available under the tradename Gantrez ES-225) and the butyl monoester of the methyl vinyl ether-maleic acid copolymer (commercially available under the tradename Gantrez ES 425).

Other suitable acid resins include acrylates copolymer, benzoic acid/phthalic anhydride/pentaerythritol/neopentyl glycol/palmitic acid copolymer, crotonic acid/vinyl neodecanoate copolymer, octylacrylamide/acrylates/butylaminoethyl methacrylate copolymer, polyacrylic acid, PVP/ethyl methacrylate/methacrylic acid copolymer, PVP/vinyl acetate/itaconic acid copolymer, shellac, styrene/maleic anhydride copolymer, vinyl acetate/crotonic acid/methyacryloxybenzophenone-1 copolymer, vinyl acetate/crotonic acid/vinyl neodecanoate copolymer, or mixtures thereof.

The term "base" means either an organic alkali or an inorganic alkali. Suitable organic bases are mono-, di-, and tri- alkanolamines, where the alkanol radical has 2 to 5 carbon atoms such as mono-, di-, or triethanolamine; mono-, di-, or triisopropanolamine; or 2-amino-2-methylpropanol; or an alkanediolamine where the alkanediol radical is of 2 to 4 carbon atoms such as 2-amino-2-methylpropane-1,3-diol or 2-amino-2-ethylpropane-1,3-diol; di(methoxyethyl)-amine; or a primary, secondary, or tertiary alkylamine having a total of 5 to 10 carbon atoms such as N,N-diethylpropylamine, or morpholine. Also included are alkyl and alkylamido derivatives of 1,3-propyldiamine, 1,4-butyl diamine, and so on. Other organic amines sometimes used for resin neutralization include the PEG fatty amine series, i.e. the Ethomeen TM group from Akzo Chemical Company. Suitable inorganic bases include the metallic hydroxides, ammonium hydroxide, and the like.

The term "acid surfactant precursor" refers to an acidic, water insoluble compound which, when neutralized, exhibits the surface activity characteristic of a surfactant. Typical acid surfactant precursors in accordance with the invention include arachidonic acid, behenic acid, capric acid, caproic acrid, caprylic acid, cocaminopropionic acid, coceth-7 carboxylic acid, cocamphodipropionic acid, coconut acid, cocoyl sarcosine, corn acid, cottonseed acid, deceth-7 carboxylic acid, hydrogenated coconut acid, hydrogenated tallow acid, hydroxystearic acid, isostearic acid, lanolin acid, lauraminopropionic acid, laureth-5 carboxylic acid, lauroamphodipropionic acid, lauroyl sarcosine, linoleic acid, linolenic acid, linseed acid, myristic acid, oleyl sarcosine, oleth-3 phosphate, oleth-4 phosphate, palmitic acid, PPG-10 cetyl ether phosphate, ricinoleic acid, soy acid, stearic acid, stearoyl sarcosine, tall oil acid, tallow acid, trideceth-4 carboxylic acid acid, trideceth-7 carboxylic acid, tridecylbenzenesulfonic acid, undecanoic acid, undecylenic acid, or mixtures thereof.

The addition of the acid surfactant precursor results in the competition of the surfactant precursor and acid resin for the available base. Theoretically, a portion of the acid surfactant precursor is neutralized, becomes water soluble and manifests surface activity which assists in the solubilization of other ingredients in the composition such as fragrances, thus rendering improved clarity to the final composition and to the resulting hair fixative film. The portion of the acid form of surfactant which is not neutralized is solubilized in the alcohol portion of the carrier which aids in plasticizing the deposited hair fixative film. The acid form of surfactant also provides additional benefits such as lowering the pH of the final. composition so that it is closer to the isoelectric point of hair. This is particularly beneficial in treating chemically processed hair, that is, hair which has been treated with high alkalinity through coloring, straightening, waving, etc. This increase in environmental acidity would help restore, through absorption, some of the neutral salt linkages of hair protein conceivably making the fiber stronger.

The carrier may be alcohol alone or a mixture of water and alcohol. Suitable alcohols include $C_{2-6}$ organic alcohols such as ethanol, isopropanol, etc. In the case where the solvent carrier is an alcohol alone, about 5–99% by weight of the total composition of alcohol is suggested. The solvent carrier may also be a mixture of water and alcohol. With pump spray formulations, the composition will generally contain, by weight of the total composition, 40–95% alcohol and 5–70% water. If an aerosol is desired, the same percentages of alcohol and water are acceptable.

As mentioned above the compositions of the invention may be used for pump sprays or aerosol sprays as well as setting gels or the like. If aerosol sprays are desired, about 15–70% propellant is suggested. Suitable propellants include n-butane, hydrocarbon propellant A-17 manufactured by the Phillips 66 Company, hydrocarbon propellant A-31 also manufactured by the Phillips 66 Company, isobutane, dimethyl ether, difluoroethane, chlorodifluoroethane, chlorodifluoromethane, other chlorofluorocarbons, or mixtures thereof. Many of these propellants are manufactured by Dupont and are available under trade names as Dymel A, Dymel 152, etc. Preferred propellants are dimethyl ether, 1,1-difluoroethane, n-butane, isobutane, or mixtures thereof. Similar propellants are available from a variety of other suppliers.

The compositions of the invention may contain other ingredients which enhance its performance such as plasticizers, silicones, surfactants, lubricants, moisturizers, and the like.

Plasticizers effect flexibility to make the resin film less brittle. Although the acid surfactant precursor of the invention also causes a plasticizing effect, it may be desired to add additional plasticizer. In this case 0.01–3% plasticizer is suggested, suitable plasticizers including polysorbate 80, acetylated lanolin alcohol, cetyl acetate, propylene glycol, lauramide DEA, laneth-10 acetate, PPG-20 methyl glucose ether, and so on.

It may also be desireable to add silicones. Either volatile or nonvolatile silicones may be used. The volatile silicones may be cyclic silicones having the general formula:

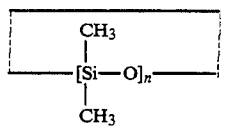

wherein n=3–7. The linear volatile polydimethylsiloxanes have from about 3 to 9 silicon atoms and have the general formula:

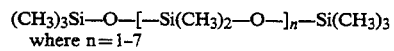

where n=1–7

As n increases over 7, the silicone becomes increasingly nonvolatile.

Silicones of the above types, both cyclic and linear, are available from Dow Corning Corporation, Dow Corning 344, 345, and 200 fluids; Union Carbide, Silicone 7202 and Silicone 7158; and Stauffer Chemical SWS-03314. The linear volatile silicones generally have viscosities of less than about 5 centipoise at 25° C. while the cyclic materials have viscosities less than about 10 centipoise. The term "volatile" means that the material has a measurable vapor pressure. Examples of nonvolatile silicones include polydimethylsiloxane gums, amine functional silicones, phenyl silicones, silicone esters, etc. Silicones, volatile or nonvolatile, may be present in the composition at a level of from 0.001–5%, preferably 0.01–1%.

It may also be desired to add surfactants. Surfactants reduce the surface tension between the liquid and air phase and allow for sprays containing a smaller droplet size. Suitable surfactants include anionic, cationic, nonionic, or amphoteric surfactants usually having an HLB of 6–12, such as PPG 28 Buteth 35, dimethicone copolyol, PEG 75 lanolin, perfluoropolymethyl isopropyl ether, polysiloxane polyether copolymers, octoxynol-9, PEG-25 hydrogenated castor oil, polyethylene glycol 25 glyceryl trioleate, PEG-20 methyl glucose ether, etc.

The composition may also contain certain moisturizing ingredients which act to provide a moisturizing effect. Suitable moisturizers include hydrolyzed silk protein, panthenol, hydrolyzed wheat protein, etc. A range of 0.0001–3% is suggested.

The preferred embodiment of the invention is a hairspray composition comprising:

a) 0.001–20% of a neutralizable hair fixative resin
b) 0.001–8% of a base
c) 0.001–5% of an acid surfactant precursor
d) 40–95% alcohol.

In addition the preferred embodiment may contain 0.01–3% of a volatile silicone and 5–70% water. Further options include 0.0001–1% moisturizer and 0.001–3% surfactant. The preferred hair fixative resins are vinyl acetate/crotonic acid/vinyl neodecanoate copolymer and octylacrylamide/acrylates/butylaminoethyl methacrylate polymer. The preferred bases are aminomethylpropanol, ammonium hydroxide or mixtures thereof. The preferred acid surfactant precursors are fatty acid sarcosines such as cocoyl sarcosine, lauroyl sarcosine, oleyol sarcosine, stearoyl sarcosine, cocaminopropionic acid, coceth-7 carboxylic acid, cocoamphodipropionic acid, deceth-7 carboxylic acid, lauraminopropionic acid, laureth-5 carboxylic acid, lauroamphodipropionic acid, oleth-3 phosphate, oleth-4 phosphate, PPG-10 cetyl ether phosphate, trideceth-4 carboxylic acid, tridecylbenzenesulfonic acid or mixture thereof. Most preferred acid form of surfactants are cocoyl sarcosine, lauroyl sarcosine, oleoyl sarcosine, stearoyl sarcosine, or mixtures thereof. The preferred alcohols are ethanol or isopropanol or mixtures thereof. Preferred silicones are volatile silicones, as cyclomethicone, or dimethicone copolyol. Preferred additional surfactants include the fatty betaines and fatty alkanokamides.

A preferred formulation is set forth below:

|  | Range % | Preferred Range % |
| --- | --- | --- |
| SDA 40B (ethanol) | 40–95 | 60–90 |
| Aminomethylpropanol | .001–8 | 0.1–1.0 |
| National Starch Resin 28–2930, Amphomer resin or mixtures | 0.001–20 | 0.01–10 |
| Dimethicone copolyol | 0.001–3 | 0.01–1 |
| Ethyl ester of hydrolyzed silk | 0.0001–1 | 0.0005–0.5 |
| Water | 5–70 | 10–40 |
| Fragrance | .01–5 | 0.1–1 |
| Oleyl or cocoyl sarcosine (acid precursor) | 0.001–5 | 0.01–3 |

The preferred formulation may, in addition, contain 0.01–5%, preferably 0.1–3% cocamidopropylbetaine, and/or alkanolamide surfactants.

The invention will be further described in connection with the following examples which are set forth for the purposes of illustration only.

EXAMPLE 1

A composition suitable for a hairspray was made as follows:

|  | w/w % |
| --- | --- |
| SD alcohol 40B | qs 100 |
| Aminomethylpropanol | 0.66 |
| National Starch Resyn 28-2930 | 4.5 |
| National Starch Amphomer resin | 1.5 |
| Dimethicone copolyol | 0.3 |
| Ethyl ester of hydrolyzed silk | 0.0001 |
| Cocamidopropyl betaine | 0.1 |
| Fragrance | 0.3 |
| Water | 12.8 |

The above formulation was mixed with two different acid form surfactants as follows:

|  | 1 | 2 | 3 |
| --- | --- | --- | --- |
|  | 99.0 | 99.0 | 99.0 |
| 10% cocoyl sarcosine in alcohol | 1.0 | — | — |
| 10% oleoyl sarcosine in alcohol | — | 1.0 | — |
| SD alcohol 40B (control) | — | — | 1.0 |

The above three compositions were sprayed on glass to observe the film obtained. Immediately after spraying, 1, 2, and 3 developed clouds upon drying on glass. 1 and 2, however, showed improved clarity over 3.

The level of acid form of surfactant was increased as follows:

|  | 4 | 5 | 6 |
| --- | --- | --- | --- |
|  | 99.5 | 99.5 | 99.5 |
| Cocoyl sarcosine (100%) | 0.5 | — | — |
| Oleoyl sarcosine (100%) | — | 0.5 | — |
| SD alcohol 40-B (control) | — | — | 0.5 |

The pH of 4 was 7.11, the pH of 5 was 7.18 and the pH of 6 7.39. These results illustrate that the acid surfactant precursor causes the composition to have increased acidity. Compositions 4, 5, and 6 were sprayed on glass plate. Compositions 4 and 5 provided a virtually clear film while 6 was cloudy on glass. Series 1–6 also showed that the formulas with the acid surfactant precursor provided increased rigidity to hair which should give better hold, rendered easier combability to hair and reduced the raspiness, i.e. gave the hair a less dry, more favorable texture. These results confirm that the composition of the invention provides an improvement over the balanced properties of the unmodified composition.

While the invention has been described in connection with the preferred embodiment, it is not intended to limit the scope of the invention to the particular form set forth, but, on the contrary, it is intended to cover such alternatives, modifications, and equivalents as may be included within the spirit and scope of the invention as defined by the appended claims.

We claim:

1. A hairspray composition comprising:
   a) 0.001–20% of a neutralizable hair fixative resin,
   b) 0.001–8% of a base, and
   c) 0.001–5% of an acid surfactant precursor selected from the group consisting of cocoyl sarcosine, lauroyl sarcorsine, oleoyl sarcosine, stearoyl sarcosine, or mixtures thereof,
   in an alcohol or aqueous/alcohol carrier.

2. The composition of claim 1 wherein the base is an organic base or an inorganic base.

3. The composition of claim 2 wherein the neutralizable hair fixative resin is the monoethyl ester of methyl vinyl ether-maleic acid copolymer, the butyl monoester of the methyl vinyl ether-maleic acid copolymer, acrylates copolymer, benzoic acid/phthalic anhydride/pentaerythritol/neopentyl glycol/palmitic acid copolymer, crotonic acid/vinyl neodecanoate copolymer, octylacrylamide/acrylates/butylaminoethyl methacrylate copolymer, polyacrylic acid, PVP/ethyl methacrylate/methacrylic acid copolymer, PVP/vinyl acetate/itaconic acid copolymer, shellac, styrene/maleic anhydride copolymer, vinyl acetate/crotonic acid/methyacryloxybenzophenone-1 copolymer, vinyl acetate/crotonic acid/vinyl neodecanoate copolymer, or mixtures thereof.

4. The composition of claim 3 wherein the base is an organic base.

5. The composition of claim 4 wherein the base is an organic base selected from the group consisting of mono-, di-, and trialkanolamines, where the alkanol radical has 2 to 5 carbon atoms such as mono-, di-, or triethanolamine; mono-, di-, or triisopropanolamine; or 2-amino-2-methylpropanol; or an alkanediolamine where the alkanediol radical is of 2 to 4 carbon atoms such as 2-amino-2-methylpropane-1,3-diol or 2-amino-2-ethylpropane-1,3-diol; di(methoxyethyl)-amine; or a primary, secondary, or tertiary alkylamine having a total of 5 to 10 carbon atoms such as N,N-diethylpropylamine, morpholine, or alkyl and alkylamido derivatives of 1,3-propyldiamine or 1,4-butyl diamine.

6. The composition of claim 5 comprising 40–95% alcohol.

7. The composition of claim 6 comprising 60–90% alcohol and 5–70% water.

8. The composition of claim 7 wherein the alcohol is a $C_{2-6}$ organic alcohol.

9. The composition of claim 8 wherein the alcohol is ethanol, isopropanol, or mixtures thereof.

10. The composition of claim 9 further comprising and ingredient selected from the group consisting of propellant, plasticizer, silicone, surfactant, moisturizer, or mixtures thereof.

11. A hairspray composition comprising:
   a) 0.001–20% of a neutralizable hair fixative resin
   b) 0.001–8% of a base
   c) 0.001–5% of an acid surfactant precursor selected from the group consisting of cocoyl sarcosine, lauroyl sarcorsine, oleoyl sarcosine, stearoyl sarcosine, or mixtures thereof
   d) 40–95% alcohol
   e) 0.01–3% volatile silicone
   f) 5–70% water.

12. The composition of claim 11 further comprising 0.0001–1% moisturizer.

13. The composition of claim 12 further comprising 0.001–3% surfactant.

14. The composition of claim 13 wherein the volatile silicone is cyclomethicone or dimethicone copolyol.

15. The composition of claim 14 wherein the acid surfactant precursor is cocoyl sarcosine or oleoyl sarcosine.

16. The composition of claim 15 wherein the resin is vinyl acetate/crotonic acid/vinyl neodecanoate copolymer, octylacrylamide/acrylates/butylaminoethyl methacrylate polymer, or mixtures thereof.

17. The composition of claim 16 wherein the base is aminomethylpropanol.

18. The composition of claim 17 wherein the alcohol is ethanol, isopropanol, or mixtures thereof.

19. A method for styling hair comprising applying to the hair the composition of claim 1.

* * * * *